United States Patent
Müller-Rees et al.

(10) Patent No.: US 9,200,248 B2
(45) Date of Patent: *Dec. 1, 2015

(54) BIOREACTOR COMPRISING A SILICONE COATING

(75) Inventors: Christoph Müller-Rees, Pullach (DE); Rupert Pfaller, Munich (DE)

(73) Assignee: Wacker Chemie AG, Munich (DE)

(*) Notice: Subject to any disclaimer, the term of this patent is extended or adjusted under 35 U.S.C. 154(b) by 0 days.

This patent is subject to a terminal disclaimer.

(21) Appl. No.: 13/389,333

(22) PCT Filed: Aug. 6, 2010

(86) PCT No.: PCT/EP2010/061491
§ 371 (c)(1), (2), (4) Date: Feb. 7, 2012

(87) PCT Pub. No.: WO2011/015655
PCT Pub. Date: Feb. 10, 2011

(65) Prior Publication Data
US 2012/0135514 A1    May 31, 2012

(30) Foreign Application Priority Data
Aug. 7, 2009  (DE) .................. 10 2009 028 338

(51) Int. Cl.
*C12M 1/00* (2006.01)
(52) U.S. Cl.
CPC ............... *C12M 39/00* (2013.01); *C12M 21/02* (2013.01)
(58) Field of Classification Search
CPC .............................. C12M 21/02; C12M 39/00
USPC ............................................ 435/283.1–309.4
See application file for complete search history.

(56) References Cited

U.S. PATENT DOCUMENTS

| | | | |
|---|---|---|---|
| 3,702,778 A | 11/1972 | Mueller et al. | |
| 2001/0021529 A1 | 9/2001 | Takagi | |
| 2003/0073231 A1 | 4/2003 | Dutil | |
| 2004/0050297 A1* | 3/2004 | Kobayashi et al. | 106/287.14 |
| 2004/0210024 A1 | 10/2004 | Schafer et al. | |
| 2004/0254325 A1 | 12/2004 | Kuepfer et al. | |
| 2005/0227092 A1* | 10/2005 | Yamaya et al. | 428/447 |
| 2007/0048848 A1 | 3/2007 | Sears | |
| 2008/0311649 A1 | 12/2008 | Cloud et al. | |
| 2009/0011492 A1 | 1/2009 | Berzin | |
| 2009/0143496 A1 | 6/2009 | Ziche | |
| 2010/0190227 A1* | 7/2010 | Dauth et al. | 435/168 |
| 2011/0020879 A1 | 1/2011 | Isobe et al. | |

FOREIGN PATENT DOCUMENTS

| | | | |
|---|---|---|---|
| CN | 1737107 A | | 2/2006 |
| DE | 4416069 A1 | | 10/1995 |
| DE | 198 50 607 A1 | | 5/2000 |
| DE | 102005025118 A1 | | 1/2007 |
| DE | 10 2009 029 792 A1 | | 12/2010 |
| EP | 1412416 B1 | | 9/2004 |
| EP | 1489129 B1 | | 4/2006 |
| GB | 1307001 | | 2/1973 |
| GB | 2118572 | | 11/1983 |
| JP | 3-251170 | | 11/1991 |
| JP | 2006-349557 | | 12/2006 |
| JP | 2007124971 A2 | | 5/2007 |
| JP | 2009-60876 | | 3/2009 |
| WO | 0194487 A2 | | 12/2001 |
| WO | WO 2004/108881 A2 | | 12/2004 |
| WO | 2006058656 A2 | | 6/2006 |
| WO | WO 2007/129327 A1 | | 11/2007 |
| WO | 2008055190 A2 | | 5/2008 |
| WO | 2008132196 A1 | | 11/2008 |
| WO | 2008145719 A1 | | 12/2008 |
| WO | WO 2009/037683 A1 | | 3/2009 |
| WO | WO 2009/091048 A1 | | 7/2009 |

OTHER PUBLICATIONS

Schumacher, et al., James F., "Engineered antifoulding microtopographies—effect of feature size, geometry, and roughness on settlement of zoospores of the green alga Ulva," Biofouling, 2007, 23 (1), pp. 55-62.
Winnacker/Küchler, "Chemische Technik: Prozesse und Produkte, vol. 5: Organische Zwischenverbindungen, Polymere", pp. 1095-1213, Wiley-VCH Weinheim (2005).
English Abstract corresponding to Winnacker/Küchler, "Chemische Technik: Prozesse und Produkte, vol. 5: Organische Zwischenverbindungen, Polymere", pp. 1095-1213, Wiley-VCH Weinheim (2005).
Alvarez, C., International Search Report dated Jan. 27, 2011, for International Application No. PCT/EP2010/061491.
English language patent abstract corresponding to DE 198 50 607 A1.
Shi Hang et al. (2008) Study on New Silicone Marine Anti-fouling Coatings. Silicone Material, vol. 22, issue 6, pp. 339-343. (Contains English language abstract).
English language patent abstract corresponding to JP 2007124971 A2.
Non-Final OA dated Dec. 4, 2012 for U.S. Appl. No. 13/389,317.
Amendment filed Apr. 5, 2013 for U.S. Appl. No. 13/389,317.
Non-Final OA dated Jul. 18, 2013 for U.S. Appl. No. 13/389,317.
Amendment filed Oct. 18, 2013 for U.S. Appl. No. 13/389,317.
Non-Final OA dated Jan. 6, 2014 for U.S. Appl. No. 13/389,317.
Oliveira, R., et al., "The Role of Hydrophobicity in Bacterial Adhesion," Hydrophobicity and Adhesion, BioLine 2001, pp. 11-22.
Final Office Action for U.S. Appl. No. 13/389,317 dated Sep. 26, 2014.

* cited by examiner

Primary Examiner — Nathan Bowers
Assistant Examiner — Lydia Edwards
(74) Attorney, Agent, or Firm — RatnerPrestia

(57) ABSTRACT

The invention relates to a bioreactor for cultivating phototrophic organisms in an aqueous culture medium. The reactor parts and/or fittings that come into contact with the culture medium are entirely or partially coated with a silicone layer, and the surface of the silicone layer has a contact angle to the water of at least 100°.

7 Claims, No Drawings

BIOREACTOR COMPRISING A SILICONE COATING

CROSS REFERENCE TO RELATED APPLICATIONS

This application is the national phase filing of international patent application No. PCT/EP2010/061491, filed 6 Aug. 2010, and claims priority of German patent application number 10 2009 028 338.2, filed 7 Aug. 2009, the entireties of which applications are incorporated herein by reference.

FIELD OF THE INVENTION

The invention relates to a bioreactor that is provided with an antifouling coating, method of providing bioreactors with an antifouling coating, and the use of silicones for providing bioreactors with an antifouling coating.

BACKGROUND OF THE INVENTION

The economic cultivation of phototrophic microorganisms (microalgae, cyanobacteria, purple bacteria) on an industrial scale has not yet been solved, owing to the problems of light supply, monoseptic culture conditions and scaling-up. To date, no universal standard system is available for the large-scale cultivation of phototrophic microorganisms. Of the many tens of thousands of representatives of phototrophic microorganisms, at present only a few dozen are produced in relatively large amounts, and these are generally produced in open systems, which are not free from contamination. To date, the culture conditions of phototrophic microorganisms, in pilot-scale production in closed reactors, cannot be kept constant for an extended period, as the phototrophic microorganisms that form in a culture phase are deposited on the reactor walls, which leads to fluctuations in the amount of light supplied to the culture medium and to variable mixing of the culture medium. Algal deposits are often caused by stress conditions (e.g. through shearing) during cultivation, the causes of which can be uncontrolled growth conditions (e.g. light, temperature in open-pond and closed reactors) of the microorganisms or induction of the production of valuable substances by the phototrophic organisms (e.g. astaxanthin, beta-carotene).

A closed photobioreactor for cultivating algae is known from WO 2008/055190 A2. The materials used are glass or plastics such as polyethylene, PET, polycarbonate. Detaching microorganisms from the surfaces of bioreactors by means of ultrasound is described in DE 10 2005 025 118 A1. In US 2003/0073231 A1 and US 2007/0048848 A1, deposits are removed by mechanical means, for example brushing. These are relatively laborious methods, which are not arbitrarily scalable. In DE 44 16 069 A1 it is recommended to provide light-conducting fibers used for illuminating bioreactors with a smooth surface. US 2008/0311649 A1 proposes increasing the flow rate of the algae-containing medium in tubular bioreactors, to prevent deposition of the algae. This has the disadvantage that the culture parameters with respect to flow rate can no longer be set independently.

In WO 2008/132196 A1, crosslinkable polyorganosiloxane-polyoxyalkylene copolymers are recommended as antifouling coating in the marine area, in particular for coating metal or concrete, for example ships' hulls, buoys, drilling rigs. Later in this publication there is discussion of GB 1307001, which describes the coating of hulls with silicone resins to prevent fouling, and of U.S. Pat. No. 3,702,778, which describes the coating of hulls with silicone rubber. It can be seen from WO 2008/132196 A1 that in both cases effective prevention of fouling is only achieved at relatively high flow rate on the hull. To prevent fouling of underwater structures, it is recommended in WO 01/94487 A2 to apply glass-like interpenetrating polymer networks based on silanol-terminated silicones and alkoxy-functionalized siloxanes, together with two separable agents, at least one of which grafts onto the glass matrix. Silicone coatings are described in this document as being unstable in a marine environment, with the disadvantage that the coating must be renewed frequently. In Biofouling, 2007, 23(1), 55-62 it is recommended to apply silicone-based antifouling paint films on hulls in particular patterns. Paints that only contain silicones are described as not inherently antifouling. In WO 2008/145719 A1, transparent LED plastic moldings are used for illuminating photoreactors. For this, it is preferable to use moldings in which LEDs are embedded in a silicone molded article.

SUMMARY OF THE INVENTION

Against this background, the problem to be solved was to improve bioreactors for cultivation of microorganisms, so that fouling with microorganisms on the reactor parts coming into contact with the culture medium is largely prevented, and any fouling that does occur can be removed inexpensively. The solution should not have a negative effect on product quality, it should be up-scalable, and should be capable of universal application, independently of the process parameters required for cultivation.

The invention relates to a bioreactor for cultivating phototrophic organisms in an aqueous culture medium, in which the reactor parts and/or reactor fittings that come into contact with the culture medium are coated completely or partially with a silicone layer, wherein the surface of the silicone layer has a contact angle with water of at least 100°.

DETAILED DESCRIPTION OF THE INVENTION

The bioreactor is suitable for the cultivation of phototrophic macro- or microorganisms. Phototrophic organisms are designated as those that require light and carbon dioxide, or optionally another carbon source as well, for growth. Examples of phototrophic macroorganisms are macroalgae, plants, mosses, plant cell cultures. Examples of phototrophic microorganisms are phototrophic bacteria such as purple bacteria and phototrophic microalgae including cyanobacteria. Preferably the bioreactor is used for the cultivation of phototrophic microorganisms, especially preferably the cultivation of phototrophic microalgae.

The bioreactor can be a closed reactor or an open reactor, in each case of any desired shape. For example, in the case of open reactors it is possible to use tanks or so-called "open ponds" or "raceway ponds". Closed reactors are preferred as bioreactors. The closed bioreactors can be for example plate-type bioreactors, tubular bioreactors, (bubble) column bioreactors or hose-type bioreactors. Plate-type bioreactors consist of perpendicular or slanting brick-shaped plates, with a large number of plates joined together to form a relatively large reactor system. Tubular bioreactors consist of a tube system, which can be arranged vertically or horizontally or at any angle in between, and the tube system can be very long, preferably up to several hundred kilometers. The culture medium is then transported through the tube system, preferably by means of pumps or by the air-lift principle. The column bioreactor consists of a closed, cylindrical vessel, which is filled with the culture medium. In bioreactors of this type, a mixture of air and carbon dioxide or also carbon dioxide is introduced, and the ascending bubble column provides mixing of the culture medium. Hose-type reactors comprise a reactor system that consists of a single hose of any length or a large number of hoses of any length.

The bioreactors are preferably made of transparent or translucent materials. Transparent materials are those that let through at least 80% of the light in the spectral range from 400 nm to 1000 nm. Translucent materials are those that let through at least 50% of the light in the spectral range from 400 nm to 1000 nm, for example glass or plastics such as polymethylmethacrylate (Plexiglas), polyesters such as PET, polycarbonate, polyamide, polystyrene, polyethylene, polypropylene, polyvinyl chloride. For nontransparent photobioreactors it is possible to use the aforesaid plastics, but also steel or special steel. Reactor volumes of any size can be selected.

Reactor parts mean the reactor walls including reactor bottom and reactor cover and structure-forming elements in the culture medium, e.g. baffles. In tubular, plate-type and hose-type reactors, the tubes, plates and hoses correspond to the reactor walls.

The bioreactors are equipped with reactor fittings; for example, with feed lines for filling and supply of nutrients, and with discharge lines for product separation and discharge. For cooling and heating, the bioreactors can optionally be equipped with heating/cooling devices such as heat exchangers. Moreover, the bioreactors can also contain stirring devices and pumps for mixing. Bioreactors are often also equipped with devices for artificial illumination. Further examples of reactor devices are measuring and control instruments for monitoring operation.

Silicones suitable for providing bioreactors with an antifouling coating are for example condensation-crosslinking silicones (silicone rubbers), addition-crosslinking silicones (silicone rubbers), silicone hybrid polymers, silicone resins and/or silicone gels, provided the surface of the films thereof has a contact angle of at least 100° with water. Transparent or translucent silicones are preferred. Transparent silicones are to be understood as silicones whose films, as a coating with a layer thickness of 10 µm, let through at least 80% of the light in the spectral range from 400 nm to 1000 nm. Translucent silicones are to be understood as those whose films, as a coating with a layer thickness of 10 µm, let through at least 50% of the light in the spectral range from 400 nm to 1000 nm.

Condensation-crosslinking silicone rubber systems contain a) organopolysiloxanes with condensable end groups, b) optionally per molecule, at least three organosilicon compounds having silicon-bonded hydrolyzable groups, and c) condensation catalysts.

Suitable crosslinked silicone rubbers, which crosslink by a condensation reaction, are room-temperature crosslinking 1-component systems, so-called RTC-1 silicone rubbers. The RTC-1 silicone rubbers are organopolysiloxanes with condensable end groups, which in the presence of catalysts undergo crosslinking by condensation at room temperature. The commonest are dialkyl polysiloxanes of structure $R_3SiO[-SiR_2O]_n-SiR_3$ with a chain length of n>2. The alkyl residues R can be identical or different and generally have 1 to 4 carbon atoms and can optionally be substituted. The alkyl residues R can also be partially replaced with other residues, preferably with aryl residues, which optionally are substituted, and where the alkyl (aryl) groups R are partially exchanged with groups capable of condensation crosslinking, for example alcohol (alkoxy system), acetate (acetic acid system), amine (amine system) or oxime residues (oxime system). Crosslinking is catalyzed by suitable catalysts, for example tin or titanium catalysts.

Suitable crosslinked silicone rubbers, which crosslink by a condensation reaction, are also room-temperature crosslinking 2-component systems, so-called RTC-2 silicone rubbers. RTC-2 silicone rubbers are obtained by condensation crosslinking of organopolysiloxanes multiply substituted with hydroxyl groups in the presence of silicic acid esters. As crosslinking agent, it is also possible to use alkyl silanes with alkoxy (alkoxy system), oxime (oxime system), amine (amine system) or acetate groups (acetic acid system), which crosslink in the presence of suitable condensation catalysts, for example tin or titanium catalysts, with the hydroxyl group-terminated polydialkylsiloxanes.

Examples of the polydialkylsiloxanes contained in RTC-1 and RTC-2 silicone rubber are those with the formula $(OH)R_2SiO[-SiR_2O]_n-SiR_2(OH)$ with a chain length of n>2, wherein the alkyl residues R can be identical or different, and the R residues have the meaning given above. Preferably the polydialkylsiloxanes contain terminal OH groups, which crosslink at room temperature with the silicic acid esters or the system alkyl silane/tin(titanium) catalyst.

Examples of the alkyl silanes (with hydrolyzable groups) contained in RTC-1 and RTC-2 silicone rubbers are those with the formula $R_aSi(OX)_{4-a}$, with a=1 to 3 (preferably 1), and X in the meaning of R' (alkoxy system), C(O)R' (acetic acid system), N=CR'$_2$ (oxime system) or NR'$_2$ (amine system), where R' denotes a monovalent hydrocarbon residue with 1 to 6 carbon atoms.

Addition-crosslinking silicone rubber systems contain a) organosilicon compounds which have residues with aliphatic carbon-carbon multiple bonds, b) optionally organosilicon compounds with Si-bonded hydrogen atoms or instead of a) and b)

c) organosilicon compounds which have residues with aliphatic carbon-carbon multiple bonds and Si-bonded hydrogen atoms, d) the addition of Si-bonded hydrogen to catalysts promoting aliphatic multiple bond formation and e) optionally the addition of Si-bonded hydrogen to agents delaying aliphatic multiple bond formation at room temperature.

Suitable addition-crosslinked silicone rubbers are room-temperature crosslinking 1-component systems, so-called addition-crosslinking RTC-1 silicone rubbers, room-temperature crosslinking 2-component systems, so-called addition-crosslinking RTC-2 silicone rubbers or also room-temperature crosslinking multicomponent systems. The crosslinking reaction can be initiated cationically, by means of corresponding catalysts, or radically, by means of peroxides, or by radiation, in particular UV radiation, or thermally.

Addition-crosslinking RTC-2 silicone rubbers are obtained by crosslinking, catalyzed with Pt-catalysts, of multiply ethylenically unsaturated groups, preferably vinyl groups, of substituted organopolysiloxanes with organopolysiloxanes multiply substituted with Si—H groups in the presence of platinum catalysts.

Preferably one of the components consists of dialkylpolysiloxanes of the structure $R_3SiO[-SiR_2O]_n-SiR_3$ with n≥0, wherein the R residues have the meaning given above. Generally R is an alkyl residue with 1 to 4 carbon atoms, wherein the alkyl residues can be replaced completely or partially with aryl residues such as the phenyl residue, and is replaced at one or both ends of one of the terminal R residues with a polymerizable group such as the vinyl group. R residues in the siloxane chain, also in combination with the R residues of the end groups, can also partially be replaced with polymerizable groups. Vinyl end-blocked polydimethylsiloxanes of the structure $(CH_2=CH_2)R_2SiO[-SiR_2O]_n-SiR_2(CH_2=CH_2)$ are preferably used.

The second component contains an Si—H-functional crosslinking agent. The polyalkylhydrogensiloxanes usually employed are copolymers of dialkylpolysiloxanes and polyalkylhydrogensiloxanes with the general formula $R''_3SiO[-SiR_2O]_n-[SiHRO]_m-SiR''_3$ with $m \geq 0$, $n \geq 0$ and with the proviso that at least two SiH groups must be present, wherein R" can have the meaning of H or R. There are accordingly crosslinking agents with side and terminal SiH groups, whereas siloxanes with R"=H, which only possess terminal SiH groups, can also still be used for chain extension. Small amounts of an organoplatinum compound are contained as crosslinking catalyst.

Moreover, special silicone rubbers have also recently become available commercially, which are crosslinked by means of the addition reaction described, wherein special platinum complexes or platinum/inhibitor systems are activated thermally and/or photochemically and thus catalyze the crosslinking reaction.

Suitable materials also include silicone hybrid polymers. Silicone hybrid polymers are copolymers or graft-copolymers of organopolymer blocks, for example polyurethane, polyurea or polyvinyl esters, and silicone blocks, generally based on polydialkylsiloxanes of the aforementioned specification. For example, thermoplastic silicone hybrid polymers are described in EP 1412416 B1 and EP 1489129 B1, the relevant disclosure of which is also to be the subject matter of this application. Silicone hybrid polymers of this kind are designated as thermoplastic silicone elastomers (TPSE) and are available commercially. Other suitable materials are (condensation or radiation) crosslinkable silicone hybrid materials, as described in WO 2006/058656, the relevant information on which is incorporated by reference in this application.

Silicone resins are also suitable materials for the production of the transparent or translucent coating. Generally the silicone resins contain units with the general formula $R_b(RO)_c SiO_{(4-b-c)/2}$, in which b is equal to 0, 1, 2 or 3, c is 0, 1, 2 or 3, with the proviso that $b+c \leq 3$, and R with the meaning given above, which form a highly crosslinked organosilicone network structure. The silicone resins used can be solvent-free, solvent-containing or can be used as aqueous systems. Furthermore, it is also possible to use functionalized silicone resins, e.g. those functionalized with epoxy or amine groups.

Silicone gels are also suitable materials for the production of the transparent or translucent coating. Silicone gels are prepared from two castable components, which crosslink at room temperature in the presence of a catalyst. One of the components generally consists of dialkylpolysiloxanes with the structure $R_3SiO[-SiR_2O]_n-SiR_3$ with $n \geq 0$ and R with the meaning given above, generally with 1 to 4 carbon atoms in the alkyl residue, wherein the alkyl residues can be replaced completely or partially with aryl residues such as the phenyl residue, and is replaced with a polymerizable group such as the vinyl group at one or at both ends of one of the terminal R residues. Moreover, R residues in the siloxane chain, also in combination with the R residues of the end groups, can be replaced partially with polymerizable groups. Vinyl end-blocked polydimethylsiloxanes of the structure $(CH_2=CH_2)R_2SiO[-SiR_2O]_n-SiR_2(CH_2=CH_2)$ are preferably used.

The second component contains an Si—H-functional crosslinking agent. The polyalkylhydrogensiloxanes usually employed are copolymers of dialkylpolysiloxanes and polyalkylhydrogensiloxanes with the general formula $R''_3SiO[-SiR_2O]_n-[SiHRO]_m-SiR''_3$ with $m \geq 0$, $n \geq 0$ and with the proviso that at least two SiH groups must be present, wherein R" can have the meaning of H or R. Accordingly there are crosslinking agents with side and terminal SiH groups, whereas siloxanes with R"=H, which only possess terminal SiH groups, can also still be used for chain extension. Small amounts of an organoplatinum compound are contained as crosslinking catalyst. The crosslinking reaction is initiated by mixing the components, and the gel is formed. This crosslinking reaction can be accelerated by the action of heat and/or by electromagnetic radiation, preferably UV radiation.

A detailed review of silicones, their chemistry, formulation and application properties is given for example in Winnacker/Küchler, "Chemische Technik: Prozesse and Produkte, Vol. 5: Organische Zwischenverbindungen, Polymere", p. 1095-1213, Wiley-VCH Weinheim (2005).

The morphology of the surface of the silicone coating is important for the inhibition or prevention of fouling with microorganisms. The surface morphology is determined from the contact angle of said surface with water. The contact angle according to the invention is adjusted by selection of the silicone materials according to the invention. Further measures for increasing the contact angle, for example roughening of the surface (e.g. to simulate the so-called lotus effect), are preferably ignored. In fact such roughening can disturb the cultivation of phototrophic microorganisms. Surfaces with contact angles between 100° and 120° are preferred, surfaces with contact angles between 100° and 115° are especially preferred, and surfaces with contact angles between 100° and 113° are quite especially preferred. The contact angle of the surface of the silicone coating with water can be determined by methods known by a person skilled in the art, for example according to DIN 55660-2, using commercially available measuring instruments for determination of the contact angle, for example the contact angle measuring systems obtainable from the company Krüss.

The reactor parts that come into contact with the culture medium, in particular the inside surfaces of the reactor walls, are coated completely or partially, preferably completely, with the aforementioned silicones. In a preferred embodiment, the reactor fittings are also coated completely or partially with silicone. The silicones are applied in liquid form, either as pure substance, as solution or in aqueous emulsion. The viscosity of the liquid to be applied for coating is preferably from 10 mPas to 300 000 mPas.

No additives that can be released from the coating, as is usual in marine antifouling systems, are added to the silicones. Application can be by the usual techniques, preferably brushing, spraying, dipping, knife-coating, casting. Dipping and spraying are especially preferred. However, for coating tubes, other methods can also be used, e.g. sponge application, spinning, extrusion or crosshead extrusion, and for level surfaces additionally application by means of roll coating, roller coating or by the lick-roll process.

Application preferably takes place directly on the reactor parts or reactor fittings, without application of a primer coat. Generally the thickness of the coating is 10 nm to 1000 μm, preferably 1 μm to 100 μm. Optionally, to improve adhesion of the silicones, the reactor parts to be coated can be pre-treated, for example by corona treatment. Optionally the silicones can contain usual additives for promoting adhesion or usual fillers for improving the mechanical properties. These additives are preferably used in maximum amounts such that the silicone coating remains transparent or translucent.

Any organisms adhering to the coated surfaces can be removed between the cultivation cycles by spraying for example with water, ethanol or $H_2O_2$ without further mechanical treatment.

The photobioreactors coated with silicone according to the invention minimize the deposition of the phototrophic organisms that form, so that the flow conditions of the culture medium remain constant, and the ideal light input for growth remains set to maximum growth of the organisms to be cultivated. Moreover, expenditure on cleaning between individual cultivation cycles and on changing the phototrophic organisms to be cultivated is minimized. This leads to substantial economic advantages on account of shorter downtimes and lower cleaning costs.

Compared with conventional silicone-containing foul-release coatings, as used for example for coating ships' hulls, the silicones used according to the invention are characterized in that there is no need for release substances, which are released from the coating (e.g. silicone oil). Furthermore, there is no need to apply intermediate layers (primer) for better adhesion and mechanical properties of the recipes used in foul-release coatings. Achievement of contact angles with water with values of at least 100°, by using appropriate silicone materials, on the one hand reduces the accumulation of water on the silicone surface, and on the other hand substances dissolved in water, which are formed for example by stress situations during cultivation of algae, are also kept away from the surface.

The invention claimed is:

1. A bioreactor for cultivating phototrophic organisms, said bioreactor comprising: (1) an aqueous culture medium of a phototropic organism; and (2) reactor parts that come into contact with the culture medium, said reactor parts comprising a silicone coating layer in contact with the culture medium, wherein the surface of the silicone layer has a contact angle with water of at least 100°, and wherein the surface of the silicone layer largely prevents biofouling on the reactor parts coming into contact with the culture medium during the cultivation of the phototropic organisms.

2. The bioreactor as claimed in claim 1, wherein the bioreactor is a closed reactor.

3. The bioreactor as claimed in claim 1, wherein the bioreactor is a plate bioreactor, tubular bioreactor, bubble column bioreactor or hose bioreactor.

4. The bioreactor as claimed in claim 1, wherein the bioreactor is made of transparent or translucent materials.

5. The bioreactor as claimed in claim 1, wherein the reactor parts are coated with a transparent or translucent silicone layer.

6. The bioreactor as claimed in claim 1, wherein the silicone layer contains one or more silicones selected from the group consisting of condensation-crosslinking silicone elastomers, addition-crosslinking silicone elastomers, silicone hybrid polymers, silicone resins and silicone gels.

7. A method for providing a bioreactor with an antifouling coating, wherein the bioreactor comprises reactor parts that contact an aqueous culture medium of a phototropic organism, comprising the step of completely or partially coating the reactor parts that contact the culture medium with a silicone layer, wherein the surface of the silicone layer has a contact angle with water of at least 100°, and wherein the surface of the silicone layer largely prevents biofouling on the reactor parts coming into contact with the culture medium during the cultivation of the phototropic organisms.

* * * * *